United States Patent [19]

Ichinohe

[11] Patent Number: 5,385,730
[45] Date of Patent: Jan. 31, 1995

[54] LACTONE-MODIFIED SILICONE COMPOSITIONS AND COSMETIC AGENTS OR LUSTERING AGENTS CONTAINING THEM

[75] Inventor: Shoji Ichinohe, Annaka, Japan

[73] Assignee: Shin-Etsu Chemical Co., Ltd., Tokyo, Japan

[21] Appl. No.: 960,563

[22] Filed: Jan. 2, 1992

Related U.S. Application Data

[63] Continuation of Ser. No. 469,208, Jan. 24, 1990, abandoned.

[30] Foreign Application Priority Data

Jan. 26, 1989 [JP] Japan ................... 1-18456

[51] Int. Cl.$^6$ ............... A61K 7/027; A61K 47/34; C08G 77/38
[52] U.S. Cl. ................ 424/78.02; 424/78.03; 424/64; 528/26; 528/27; 528/28; 556/437; 556/450; 556/453
[58] Field of Search ............. 424/78.02, 78.03; 528/26, 27, 28; 514/772; 556/437, 450, 453

[56] References Cited

U.S. PATENT DOCUMENTS

| | | | |
|---|---|---|---|
| 4,636,552 | 1/1987 | Gay et al. | 525/63 |
| 4,894,224 | 1/1990 | Kuwata et al. | 514/789 |
| 4,925,659 | 5/1990 | Grollier et al. | 424/47 |
| 4,985,511 | 1/1991 | Wagener et al. | 528/27 |

FOREIGN PATENT DOCUMENTS

| | | | |
|---|---|---|---|
| 2005037 | 5/1969 | France . | |
| 2007788 | 1/1970 | France . | |
| 57212109 | 12/1982 | Japan | 424/78.03 |
| 61-37843 | 2/1986 | Japan . | |
| 62-187772 | 8/1987 | Japan . | |

*Primary Examiner*—Thurman K. Page
*Assistant Examiner*—Peter F. Kulkosky
*Attorney, Agent, or Firm*—Finnegan, Henderson, Farabow, Garrett & Dunner

[57] ABSTRACT

A lactone-modified silicone composition comprising a lactone-modified silicone compound of general formula (I), and a low-viscosity silicone oil of general formula (II) having a viscosity of not more than 100 cSt at 25° C., a cosmetic agent containing it, and a lustering agent containing it.

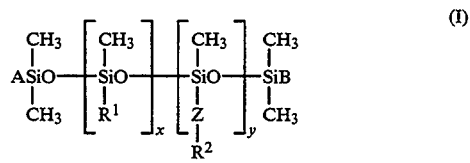

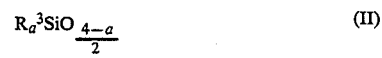

In formula (I) above, $R^1$ is the same or a different group selected from the group consisting of an alkyl group having 1 to 30 carbon atoms, a substituted or non-substituted phenyl group having 1 to 30 carbon atoms, or a phenylalkylene group having 1 to 30 carbon atoms consisting of a substituted or non-substituted phenyl group and an alkylene group having 2 or 3 carbon atoms, and wherein at least 50 wt. % of $R^1$ is an alkyl group having 1 to 30 carbon atoms;

A and B is each the same or a different group, and represents a methyl or $R^2Z$ group;

wherein $R^2$ represents a polyester group having an average molecular weight of 200 to 100,000 obtained by lactone ring opening polymerization;

z is a divalent group that connects a silicon atom to an $R^2$ group;

x is an integer of 3 to 1,000;

y is an integer of 0 to 50; and in formula (II) above,

R is a substituted or non-substituted, the same or a different, monovalent hydrocarbon group having 1 to 6 carbon atoms; and a is a number of from 1.8 to 2.3. The lactone-modified silicone composition is stable and may be smoothly spread, and it is exceptionally useful as a component for cosmetic agents and lustering agents.

9 Claims, No Drawings

LACTONE-MODIFIED SILICONE COMPOSITIONS AND COSMETIC AGENTS OR LUSTERING AGENTS CONTAINING THEM

This application is a continuation of application Ser. No. 07/469,208 filed Jan. 24, 1990 now abandoned.

BACKGROUND OF THE INVENTION

The present invention relates to a silicone composition containing a low-viscosity oil as a base oil, and more particularly to a lactone-modified silicone composition that is very uniform and stable namely, one wherein no separation of components is observed, and a cosmetic agent or lustering agent containing it.

Conventionally, paste-like or grease-like materials containing a silicone oil as a main component have been used in many industries, and recently various wax-like compositions containing a low-viscosity silicone oil have been proposed in many industries, especially in the medical and cosmetic industries, because such a low-viscosity silicone oil is excellent in its smooth spreadability on human skin and its refereshing feeling when it is used, in addition to its good features of low toxicity and little skin irritation. In these wax-like compositions, a large amount of a thickening agent made of inorganic materials such as silica flour, kaolin, talc, sericite, bentonire, etc., or organic materials such as lithium soap, aluminium soap, etc. had to be blended to change a low-viscosity oil to a paste-like or grease-like material (examples of these thickening agents are shown in *Silicone Resins*, vol. 9, of *Plastic Material Series*, published by Nikkan Kogyo Shinbun-sha).

However, the use of a large amount of a thickening agent makes it difficult to get a smooth and uniform silicone composition. It has further been pointed out that separation of the silicone oil from the composition often occurs, and thus it fails to maintain its stability.

Wax-like compositions containing a low-viscosity silicone oil have generally also not been known, because the known synthetic or natural waxes are hydrocarbons or their ester compounds, and they are not compatible with a low-viscosity silicone oil, and thus the waxes and the silicone oil separate.

Accordingly, a silicone oil having a relatively high viscosity of not less than 100 cSt at 25° C. have been used as a base oil. However, paste-like or grease-like silicone compositions using a silicone oil having a relatively high viscosity as a base oil cannot be smoothly spread, and often give a sticky feeling when they are used. Thus, it is considered that creams, sticks, ointments, or cake-like compositions using such silicone compositions did not have the needed qualities.

SUMMARY OF THE INVENTION

It is a general object of the invention to provide a silicone composition containing as a base oil a low viscosity silicone oil which is very stable in a paste-like, grease-like, or wax-like state.

It is another object of the invention to provide a cosmetic agent which may be smoothly spread, and that is stable and that is not sticky.

It is still another object of the invention to provide a lustering agent that may be smoothly spread, and that is excellent in its water-repellent properties.

It has now been found by the inventor that a specific silicone compound becomes an excellent thickening agent for a low-viscosity silicone oil, and that these and other objects of the invention are achieved by providing 1) a lactone-modified silicone composition comprising a lactone-modified silicone compound of general formula (I), and a low-viscosity silicone oil of general formula (II) having a viscosity of not more than 100 cSt at 25° C., 2) a cosmetic agent containing the lactone-modified silicone composition, and 3) a lustering agent containing the lactone-modified silicone composition.

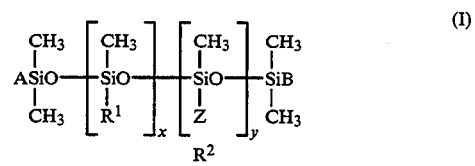

In formula (I) above,

R$^1$ is the same or a different group selected from the group consisting of an alkyl group having 1 to 30 carbon atoms, a substituted or non-substituted phenyl group having 1 to 30 carbon atoms, or a phenylalkylene group having 1 to 30 carbon atoms consisting of a substituted or non-substituted phenyl group and an alkylene group having 2 or 3 carbon atoms, and wherein at least 50 wt. % of R$^1$ is an alkyl group having 1 to 30 carbon atoms.

A and B is each the same or a different group, and represents a methyl or R$^2$Z group, wherein R$^2$ represents a polyester group having an average molecular weight of 200 to 100,000 obtained by lactone ring opening polymerization, Z is a divalent group that connects a silicon atom to an R$^2$ group, x is an integer of 3 to 1,000, and y is an integer of 0 to 50.

In formula (II) above,

R is a substituted or non-substituted, the same or a different, monovalent hydrocarbon group having 1 to 6 carbon atoms, and is preferably a methyl group. The a is a number of from 1.8 to 2.3, and is preferably 2. The viscosity of the silicone oil of formula (II) shall be not more than 100 cSt at 25° C., and preferably not more than 10 cSt at 25° C.

DETAILED DESCRIPTION

Any lactone-modified silicone compound which is obtained by ring opening polymerization may be preferably used as the lactone-modified silicone compound of formula (I), but a block copolymer of formula (II) or (IV) is particularly preferable from the point of compatibility with a silicone oil.

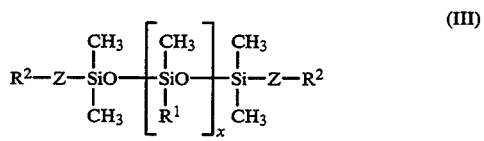

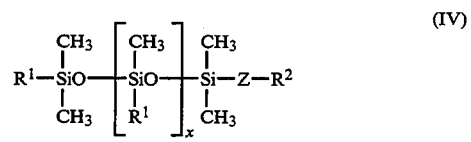

In formula (III) or (IV) above, $R^1$, $R^2$, Z and X, are the same as defined in formula (I) above.

Illustrative of Z group are those represented by the formulae:

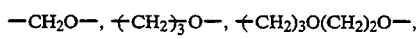

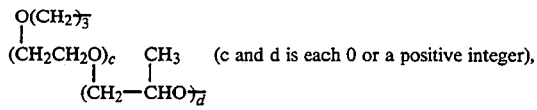 (c and d is each 0 or a positive integer),

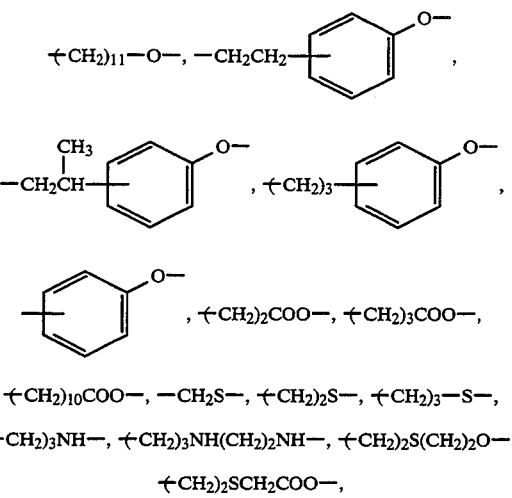

$R^2$ is a group obtained from lactone ring opening polymerization, and the lactones used in the ring opening polymerization should have not less than 4, and preferably not less than 6, carbon atoms in its ring. Illustrative of preferable lactones are lactones having more than 5 ring members, such as ε-caprolactone, δ-valerolactone, γ-butyrolactone, etc.

The preferable lactones have, for example, the following structures:

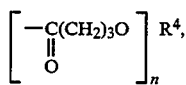

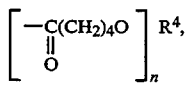

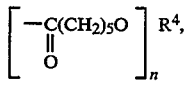

In the structures above $R^4$ is a hydrogen atom, $R^5$ (a monovalent hydrocarbon group), or

The introduction of the $ZR^2$ group to formula (I) above may be made by first synthesizing a silicone compound having a ZH group, and then polymerizing the thus-obtained silicone compound with a lactone by means of a Sn or Ti catalyst (see, for example, Japanese Patent Laid-open Publication Nos. 61-37843 and 62-187772).

The reaction of a silicone compound and a lactone is usually carried out without using any solvent, at 100° C. to 200° C., and preferably at 120° C. to 160° C. Solvents may be used in this reaction; however, usable solvents shall be limited to those which do not contain any active hydrogen atoms.

The reaction of a silicone compound having a ZH group and a lactone may also be carried out in a low-viscosity silicone oil having formula (II). The thus-obtained lactone-modified silicone compound has OH groups.

The thus-obtained lactone-modified silicone compound may be used in this invention without any modification; however, active hydrogens in the silicone compounds may optionally be blocked by acetoxylation with acetic anhydride, or by first converting the thus-obtained lactone-modified silicone compound to an alcoholate, and then converting it to an ether with an alkylhalide.

A lactone-modified silicone compound may also be synthesized by first synthesizing a polylactone having a double bond at its end (for example, allyl ether), and then by conducting a known addition reaction between the thus-obtained polylactone and a siloxane compound having SiH groups by means of a platinum catalyst.

The silicone composition of the present invention is easily obtained by first heating a lactone-modified silicone compound of formula (I) and a silicone oil of formula (II) up to a temperature not lower than the melting point of the lactone-modified silicone compound, preferably not lower than 100° C., to get a clear or translucent uniform composition, and then cooling it. As stated above, the silicone composition may be directly obtained by synthesizing a silicone compound of formula (I) in a silicone oil of formula (II).

The blending ratio of the lactone-modified silicone compound of formula (I) to the silicone oil of formula (II) may properly be chosen based on the degree of lactone modification of the lactone-modified silicone compound, the kind of silicone oil used, and the fields of uses of the silicone composition. Generally, when the degree of lactone modification is high, the uniformity and stability of the silicone composition are good, even when the blending ratio of the lactone-modified silicone compound of formula (I) is low.

The silicone composition of the invention is uniform, may be smoothly spread, and has a clear or translucent paste-like, grease-like, or wax-like appearance. These features are those which cannot be found in conventional low-viscosity silicone-containing compositions that are opaque, and that are poor in stability and spreadability. These features make the silicone composition of this invention very preferable as a component for a cosmetic agent and a lustering agent.

If the blending ratio of the lactone-modified silicone compound is increased, the resulting silicone composition becomes a hard and wax-like material that has virtually no spreadability; however, this composition is also preferable for, for example, a component for lipstick.

The silicone composition of the invention is illustrated in more detail by reference to the following examples. These examples, however, are illustrative only, and the claims are not to be construed as being limited by them.

EXAMPLE 1

To a 1-liter flask equipped with an agitator, 255 g (0.05 mole) of a silicone compound corresponding to the following mean average formula:

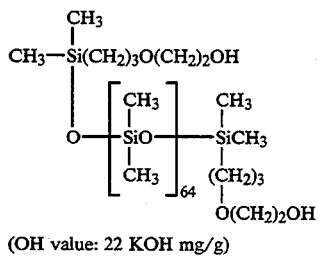

(OH value: 22 KOH mg/g)

and 228g (2 moles) of ε-caprolactone were added, and following the addition of 0.15 g of dibutyltindilaurate this feed was reacted for 10 hours at a temperature of 130° C. to 140° C. while the feed was agitated. A lactone-modified silicone compound of formula (V) having a melting point of 49° C. and a volatile loss of 0.5% at 105° C. for 3 hours was obtained.

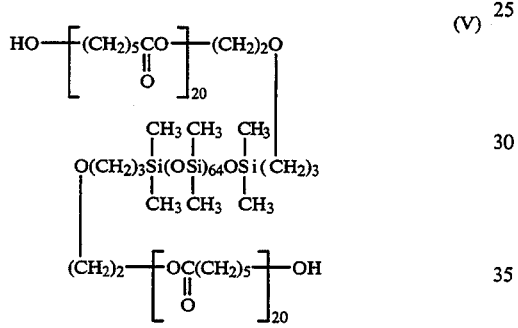
(V)

20 weight parts of the thus-obtained silicone compound of formula (V) was kneaded by a known method with 80 weight parts of a low-viscosity dimethylsilicone oil having a viscosity of 4 cSt at 25° C., and a grease-like composition having a consistency of 420 was obtained. This composition was very uniform, and very stable, and no separation of the components was observed.

EXAMPLE 2

30 weight parts of the silicone compound of formula (V) and 70 weight parts of the dimethylsilicone oil, both components being the same as those used in EXAMPLE 1, were kneaded in the same manner as described in EXAMPLE 1, and a soft and wax-like composition having a melting point of 40° C. was obtained. The uniformity and stability of thus-obtained composition were also very excellent.

EXAMPLE 3

10 weight parts of the silicone compound of formula (V) and 90 weight parts of the dimethylsilicone oil, both components being the same as those used in EXAMPLE 1, were kneaded in the same manner as described in EXAMPLE 1. The thus-obtained composition was not so stable, and separation of the dimethylsilicone oil was observed.

EXAMPLES 1 to 3 above revealed that the higher the content of a lactone-modified silicone compound in the silicone composition, the more uniform and stable the silicone composition becomes, and that the lactone-modified silicone compound is very effective in improving the uniformity and stability of the silicone composition of this invention.

To know the effect of the degree of lactone modification, the lactone-modified silicone compound of formula (V) used in EXAMPLE 1 was replaced by that of formula (VI) described below, which has a higher degree of lactone modification, and EXAMPLES 4 to 8 were conducted.

EXAMPLES 4 to 8

To a 2-liter flask equipped with an agitator, 510 g (0.1 mole) of the same silicone compound as that used in EXAMPLE 1 and 684 g (6 moles) of ε-caprolactone were added, and following the addition of 0.24 g of tetrabutyltitanate, the feed was reacted for 15 hours at a temperature of 130° C. to 140° C. while the feed was agitated. A lactone-modified silicone compound of formula (VI) having a melting point of 54° C. and a volatile loss of not more than 1% at 105° C. for 3 hours was obtained.

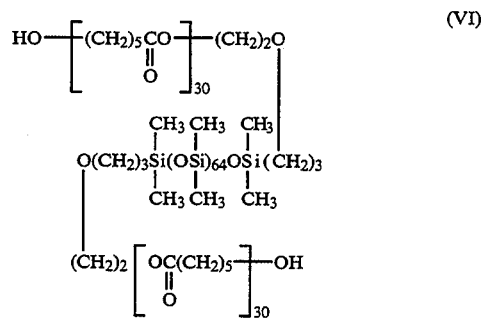
(VI)

The lactone-modified silicone compound of formula (VI) was kneaded with a low-viscosity silicone oil in the ratios shown in Table 1. The results in appearance, viscosities, consistency, and melting points of the silicone compositions thus obtained are shown in Table 1. In EXAMPLES 4 to 8, the uniformity and stability of the silicone compositions were excellent.

TABLE 1

| EXAMPLE NO. | 4 | 5 | 6 | 7 | 8 |
|---|---|---|---|---|---|
| Dimethylsilicone Oil (4 cSt) | 90 | 80 | 40 | — | — |
| Methylphenyl-silicone Oil (15 cSt) | — | — | — | 80 | 70 |
| Silicone Compound of formula (VI) | 10 | 20 | 60 | 20 | 30 |
| Appearance | Paste-like | Grease-like | Hard & wax-like | Grease-like | Soft & wax-like |
| Viscosity (at 25° C.) | 500 cp | — | — | — | — |
| Consistency | — | 320 | — | 310 | — |
| Melting Point | — | — | 52° C. | — | 45° C. |

The results shown in Table 1 show that the basic properties of the silicone composition are governed by the relative content of a lactone-modified silicone compound, and that the type or viscosity of a low-viscosity silicone oil is not so influencing. The results of EXAMPLES 3 and 4 clearly show that the high degree of the lactone modification of the silicone compound assures the uniformity and stability of the silicone composition even when the amount of the silicone compound is low.

From the foregoing description, one skilled in the art can easily ascertain the essential characteristics of this invention, and without departing from the spirit and scope thereof, can make various changes and modifications of the invention to adapt it to various uses and conditions.

I claim:

1. A uniform and stable lactone-modified silicone composition comprising between greater than 10 and 60 parts by weight of a lactone-modified silicone block copolymer of general formula (I), and between less than 90 and 40 parts by weight of a low-viscosity silicone oil of general formula (II) having a viscosity of not more than 100 cSt at 25° C.;

$$\text{ASiO}\begin{pmatrix}CH_3\\|\\CH_3\end{pmatrix}\begin{bmatrix}CH_3\\|\\SiO\\|\\R^1\end{bmatrix}_x\begin{bmatrix}CH_3\\|\\SiO\\|\\Z\\|\\R^2\end{bmatrix}_y\begin{matrix}CH_3\\|\\SiB\\|\\CH_3\end{matrix} \quad (I)$$

$$R_a{}^3SiO_{\frac{4-a}{2}} \quad (II)$$

wherein in formula (I)

R$^1$ is the same or a different group selected from the group consisting of an alkyl group having 1 to 30 carbon atoms, a substituted or non-substituted phenyl group having 1 to 30 carbon atoms, and a phenylalkylene group having 1 to 30 carbon atoms consisting of a substituted or non-substituted phenyl group and an alkylene group having 2 to 3 carbon atoms, and wherein at least 50 wt. % of R$^1$ is an alkyl group having 1 to 30 carbon atoms;

A and B is each the same or a different group, and represents a methyl or R$^2$Z group;

wherein R$^2$ represents a polyester group having a block sequence structure and having an average molecular weight of 200 to 100,000 obtained by lactone ring opening polymerization;

Z is a divalent group that connects a silicone atom to a R$^2$ group;

X is an integer of 3 to 1,000;

Y is an integer of 0 to 50; and in formula (II)

R is a substituted or non-substituted, the same or a different, monovalent hydrocarbon group having 1 to 6 carbon atoms; and a is a number of from 1.8 to 2.3.

2. A lactone-modified silicone composition according to claim 1, wherein the lactone-modified silicone compound of formula (I) is a block copolymer of formula (III) or (IV), $$R^2-Z-\begin{matrix}CH_3\\|\\SiO\\|\\CH_3\end{matrix}\begin{bmatrix}CH_3\\|\\SiO\\|\\R^1\end{bmatrix}_x\begin{matrix}CH_3\\|\\Si-Z-R^2\\|\\CH_3\end{matrix} \quad (III)$$

$$R^1-\begin{matrix}CH_3\\|\\SiO\\|\\CH_3\end{matrix}\begin{bmatrix}CH_3\\|\\SiO\\|\\R^1\end{bmatrix}_x\begin{matrix}CH_3\\|\\Si-Z-R^2\\|\\CH_3\end{matrix} \quad (IV)$$

wherein R$^1$, R$^2$, Z, and x are the same as defined in formula (I).

3. A lactone-modified silicone composition according to claim 1, wherein the lactone-modified silicone compound of formula (I) is $$HO\begin{bmatrix}(CH_2)_5CO\\||\\O\end{bmatrix}_{20}(CH_2)_2O \quad (V)$$
$$O(CH_2)_3\underset{\underset{CH_3}{|}}{\overset{\overset{CH_3}{|}}{Si}}(OSi)_{64}O\underset{\underset{CH_3}{|}}{\overset{\overset{CH_3}{|}}{Si}}(CH_2)_3$$
$$(CH_2)_2\begin{bmatrix}OC(CH_2)_5\\||\\O\end{bmatrix}_{20}OH$$

4. A lactone-modified silicone composition according to claim 1, wherein the lactone-modified silicone compound is $$HO\begin{bmatrix}(CH_2)_5CO\\||\\O\end{bmatrix}_{30}(CH_2)_2O \quad (VI)$$
$$O(CH_2)_3\underset{\underset{CH_3}{|}}{\overset{\overset{CH_3}{|}}{Si}}(OSi)_{64}O\underset{\underset{CH_3}{|}}{\overset{\overset{CH_3}{|}}{Si}}(CH_2)_3$$
$$(CH_2)_2\begin{bmatrix}OC(CH_2)_5\\||\\O\end{bmatrix}_{30}OH$$

5. A lactone-modified silicone composition according to claim 1, wherein the silicone oil of formula (II) has a viscosity of not more than 10 cSt at 25° C.

6. A lactone-modified silicone composition according to claim 1, wherein the silicone oil of formula (II) is a dimethylsilicone oil.

7. A lactone-modified silicone composition according to claim 6, wherein the dimethylsilicone oil has a viscosity of not more than 10 cSt at 25° C.

8. A cosmetic composition including a uniform and stable lactone-modified silicone composition comprising between greater than 10 and 60 parts by weight of a lactone modified silicone block copolymer of the general formula (I), and between less than 90 and 40 parts by weight of a low viscosity silicone oil of the general formula (II) having a viscosity of not more than 100 cST at 25° C.;

$$\text{ASiO}\begin{pmatrix}CH_3\\|\\CH_3\end{pmatrix}\begin{bmatrix}CH_3\\|\\SiO\\|\\R^1\end{bmatrix}_x\begin{bmatrix}CH_3\\|\\SiO\\|\\Z\\|\\R^2\end{bmatrix}_y\begin{matrix}CH_3\\|\\SiB\\|\\CH_3\end{matrix} \quad (I)$$

$$R_a{}^3SiO_{\frac{4-a}{2}} \quad (II)$$

wherein in formula (I)

R$^1$ is the same or different and is selected from the group consisting of an alkyl group having 1 to 30 carbon atoms, a substituted or non-substituted phenyl group having 1 to 30 carbon atoms, or a phenylalkylene group having 1 to 30 carbon atoms consisting of a substituted or non-substituted phenyl group and an alkylene group having 2 to 3 carbon atoms, and wherein at least 50 wt. % of $R^1$ is an alkyl group having 1 to 30 carbon atoms;

A and B are the same or different, and represent a methyl or $R^2Z$ group;

wherein $R^2$ represents a polyester group having a block sequence structure and having an average molecular weight of 200 to 100,000 obtained by lactone ring opening polymerization;

Z is a divalent group that connects a silicon atom to an $R^2$ group;

x is an integer of 3 to 1,000;

y is an integer of 0 to 50; and wherein in formula (II)

R is a substituted or non-substituted, same or different, monovalent hydrocarbon group having 1 to 6 carbon atoms; and a is a number of from 1.8 to 2.3.

9. A lustering agent including a uniform and stable lactone-modified silicone composition comprising between greater than 10 and 60 parts by weight of a lactone modified silicone block copolymer of general formula (I), and between less than 90 and 40 parts by weight of a low viscosity silicone oil of general formula (II) having a viscosity of not more than 100 cST at 25° C.;

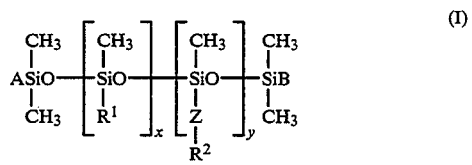

wherein in formula (I)

$R^1$ is the same or different and is selected from the group consisting of an alkyl group having 1 to 30 carbon atoms, a substituted or non-substituted phenyl group having 1 to 30 carbon atoms, or a phenylalkylene group having 1 to 30 carbon atoms consisting of a substituted or non-substituted phenyl group and an alkylene group having 2 to 3 carbon atoms, and wherein at least 50 wt. % of $R^1$ is an alkyl group having 1 to 30 carbon atoms;

A and B are the same or different, and represent a methyl or $-R^2Z$ group;

wherein $R^2$ represents a polyester group having a block sequence structure and having an average molecular weight of 200 to 100,000 obtained by lactone ring opening polymerization;

Z is a divalent group that connects a silicon atom to an $R^2$ group;

x is an integer of 3 to 1,000;

y is an integer of 0 to 50; and wherein in formula (II)

R is a substituted or non-substituted, same or different, monovalent hydrocarbon group having 1 to 6 carbon atoms; and a is a number of from 1.8 to 2.3.

* * * * *